United States Patent [19]

Novotny et al.

[11] Patent Number: 5,080,771
[45] Date of Patent: Jan. 14, 1992

[54] CAPILLARY GELS FORMED BY SPATIALLY PROGRESSIVE POLYMERIZATION USING MIGRATING INITIATOR

[75] Inventors: Milos V. Novotny, Bloomington, Ind.; Vladislav Dolnik, Brno, Czechoslovakia; Kelly A. Cobb, Bloomington, Ind.

[73] Assignee: Indiana University Foundation, Bloomington, Ind.

[21] Appl. No.: 603,983

[22] Filed: Oct. 26, 1990

[51] Int. Cl.⁵ .......................... C25B 1/00; C25B 7/00; B01D 57/02; B01D 61/42
[52] U.S. Cl. .............................. 204/182.8; 204/180.1; 204/299 R
[58] Field of Search .............. 204/182.8, 299 R, 180.1

[56] References Cited

U.S. PATENT DOCUMENTS

| | | | |
|---|---|---|---|
| 4,680,201 | 7/1987 | Hjerten | 427/230 |
| 4,863,647 | 9/1989 | Baylor, Jr. | 264/22 |
| 4,936,974 | 6/1990 | Rose et al. | 204/299 R |
| 4,997,537 | 3/1991 | Karger et al. | 204/299 R |

Primary Examiner—John Niebling
Assistant Examiner—Caroline Koestner
Attorney, Agent, or Firm—Townsend and Townsend

[57] ABSTRACT

Gels are formed in capillary tubes by electrophoretically drawing a charged polymerization initiator into a capillary tube pre-filled with monomer, crosslinking agent and catalyst. The rate of travel of the initiator is slow enough to maintain a sharp leading edge or front, thereby causing polymerization to occur in a progressive manner from one end of the capillary to the other. The shrinkage inherent in the polymerization reaction is thus compensated by fluid movement ahead of the traveling initiator front, and discontinuities in the gel which would otherwise be formed are avoided.

18 Claims, 4 Drawing Sheets

CAPILLARY GELS FORMED BY SPATIALLY PROGRESSIVE POLYMERIZATION USING MIGRATING INITIATOR

The U.S. Government has a paid-up license in this invention and the right in limited circumstances to require the patent owner to license others on reasonable terms as provided for by the terms of Grant No. PHS R01 GM 24349 awarded by the National Institute of General Medical Sciences, U.S. Public Health Service.

This invention lies in the field of gel electrophoresis, with a focus on the use of gel-filled capillaries for capillary electrophoresis.

BACKGROUND OF THE INVENTION

One of the most significant recent developments in the technology of analytical techniques for biological mixtures is the technique of capillary electrophoresis. Capillaries provide distinct advantages in the separations of such species as small peptides, proteins and nucleic acids, since they can be used to analyze extremely small samples with convenient on-line spectroscopic detection, and they permit the use of high voltages, thereby achieving separations at relatively high speed.

The use of a gel as the separation medium in the capillary combines the advantages of capillary electrophoresis with the known capabilities of gel electrophoresis. Due to their unique geometry, however, capillaries present a distinct challenge, particularly in the preparation of the gel in the capillary. One troublesome factor is the difficulty of obtaining uniform gel consistency and concentration throughout the capillary. These are important in achieving component resolution and reproducibility, and are therefore important considerations in achieving optimal use of the technique, particularly with capillaries of very narrow bore. This is difficult to achieve with gels in capillaries, since the shrinkage of the gel, which is an inherent result of the polymerization reaction, causes gaps in the gel, particularly bubble-like open spaces, generally of microscopic dimensions, which create deviations from gel uniformity. Such discontinuities lead to current drop and disruption of the applied electric field gradient during electrophoresis, which in turn lower the efficiency, reliability and reproducibility of the separation.

Although techniques have been proposed to overcome this problem, they tend to require materials, equipment or procedures, which are not generally used in connection with capillaries, gel preparation or electrophoresis, and give varying results. The present invention addresses this need, in a simple, efficient, reproducible and reliable manner.

SUMMARY OF THE INVENTION

It has now been discovered that gel-filled capillaries lacking the discontinuities which commonly arise during the gel formation process can be prepared by using an electric field, in a manner analogous to an electrophoretic procedure, to introduce a charged polymerization initiator into one end of the capillary and drawing it continuously along the length of the capillary until it has pervaded the entire interior volume of the capillary, the capillary having been pre-filled with a liquid solution of all gel-forming materials with the exception of the initiator. The initiator entering the tube is led by a front which travels longitudinally through the capillary at a slow, substantially steady linear velocity in the axial direction. Polymerization of the gel at any given point in the capillary thereby begins when the front first passes that point, and proceeds to completion under the continued exposure to initiator moving past it.

In this specification, the term "front" refers to an interface which separates the portion of the capillary interior in which the initiator is present from that portion in which it is substantially absent. Although the interface will in most cases be less than a perfectly sharp boundary, broadening or blurring of the interface can be minimized by appropriate control of the migration conditions in the same sense as in electrophoretic separations. The location of the interface is generally defined by the fact that polymerization occurs on the initiator side and does not occur on the opposing side.

Shrinkage of the gel materials which occurs as a result of the polymerization reaction is substantially if not entirely limited to the region located immediately behind the traveling initiator front, drawing the as yet unpolymerized liquid backward in unidirectional manner and effectively eliminating stress in the gel-containing region as well as the tendency to form irregularities or discontinuities in the gel thus formed. The procedure is conducted under conditions rendering the gel-forming material in the capillary substantially free of electroosmotic flow. Furthermore, in preferred embodiments, one of the components of the gel-forming mixture, bearing a charge opposite to that of the initiator, serves as a counter-ion during the initiator introduction, entering the capillary from the other end as a means of maintaining the level of that component throughout the entire capillary for the duration of the polymerization procedure.

Further features, aspects, and embodiments of the invention will be apparent from the description which follows.

DETAILED DESCRIPTION OF THE INVENTION AND PREFERRED EMBODIMENTS

Figure 1:
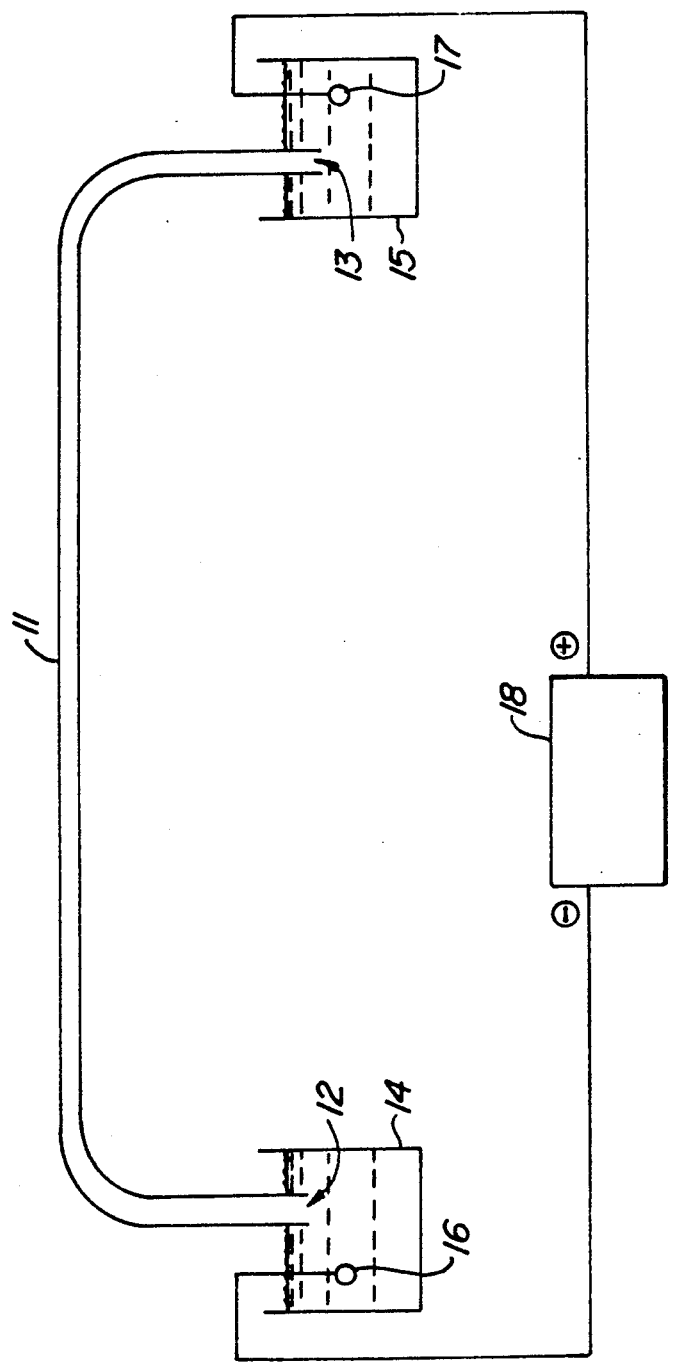
FIG. 1 is a diagrammatic representation illustrating an embodiment of the invention, in which a capillary tube filled with gel-forming material is arranged for introduction of polymerization initiator in one end by the imposition of an electric potential.

Various gels are used in gel electrophoresis, and are applicable to the present invention, the choice of gel not being critical to the invention. Gels of primary interest, however, are polyacrylamide gels, in view of the known applicability of this material to the size fractionation of charged macromolecules such as proteins and nucleic acids, as well as small peptides. Mixtures of polyacrylamide with other gel materials such as agarose are also of interest.

The gel-forming material generally includes a crosslinking agent. A wide variety of crosslinking agents are known and suitable for use in the context of this invention. Examples of crosslinking agents capable of use in acrylamide polymerization are N,N'-methylenebisacrylamide, N,N'-(1,2-dihydroxyethylene)bisacrylamide, N,N'-diallyltartardiamide, N,N'-cystaminebisacylamide, and N-acryloyltris(hydroxymethyl)aminomethane. A preferred crosslinking agent is N,N'-methylenebisacrylamide.

The concentrations of gel monomer and crosslinking agent are not critical and may vary considerably. The appropriate or optimum choice in any particular case will depend on the composition of the mixtures sought to be separated by the finished gel, as well as the dimensions of the capillary and the conditions under which the separation is to be performed. In most cases, best results will be obtained using aqueous solutions of gel forming materials in which the concentration of the gel-forming monomer and the crosslinking agent combined range from about 0.05% to about 20% by weight, preferably from about 2% to about 8% by weight. Likewise, the forming monomer and cross-linking agent will in most cases range from about 0.5% to about 20% by weight, preferably from about 2% to about 6% by weight. The combined concentration of monomer and crosslinking agent is the variable commonly referred to in the literature as "T," while the proportion of crosslinking agent to the total is the variable referred to as "C."

Polymerization is generally done in the presence of a polymerization catalyst, which in the case of polyacrylamide formation is a base catalyst. The actual base used is not critical, and any of a variety of bases known as polymerization catalysts may be used. Prime examples for polyacrylamide are amine bases such as N,N,N',N'-tetramethylethylenediamine, β-dimethylaminopropionitrile, and triethanolamine. Preferred among these are N,N,N',N'-tetramethylethylenediamine ("TEMED" or "TMEDA") and triethanolamine. The quantity of base may also vary, although in most cases, the base will generally be used in a concentration ranging from about 0.01 M to about 1M, preferably from about 0.03M to about 0.3M.

The polymerization initiator which is introduced into the capillary by mobilization under the influence of the electric field is any charged species which will initiate the polymerization reaction. Neither the chemical nature nor mechanism of the initiator are critical. In most cases, however, the initiator will be a free radical initiator. Preferred free radical initiators are peroxides, persulfates and azo compounds. Examples are benzoyl peroxide, tert-butyl peroxide, tert-butyl hydroperoxide, tert-butyl perbenzoate, cumyl peroxide, acetyl peroxide, lauroyl peroxide, 2,2'-azobisisobutyronitrile, phenyl-azo-triphenylmethane and persulfates such as potassium persulfate and ammonium persulfate. Preferred among these, particularly in aqueous systems, are the persulfates, particularly ammonium persulfate.

In accordance with the invention, the initiator is omitted from the components of the gel-forming material in the capillary tube prior to the imposition of the electric field, and held instead in solution in a reservoir. Immersed in the reservoir are one open end of the capillary and an electrode. The counter electrode and the other end of the capillary are immersed in a second reservoir. The concentration of the initiator in the first reservoir is not critical and can vary widely. In most applications, particularly those in which the initiator is persulfate ion, best results are obtained with a concentration ranging from about 0.03M to about 2.0M, preferably from about 0.1M to about 2.0M.

Negatively charged initiators such as persulfate ion will be placed in the cathodic vessel. A positively charged counter-ion will accordingly be placed in the anodic vessel for migration in the opposite direction. While the nature and identity of the counter-ion are not critical to the invention, in preferred embodiments the counter-ion will be the same base included as the catalyst in the gel-forming solution occupying the capillary. Thus, as the base in the capillary migrates under the influence of the electric field in the direction opposite that of the initiator, the depleting base is replaced by base continually being introduced from the anodic vessel. The concentration of base in the anodic vessel will generally be higher than the concentration of base initially placed in the capillary, although the actual concentration is not critical and can vary widely. In preferred embodiments the concentration of base in the anodic vessel will range from about 0.1M to about 10M, most preferably from about 0.3M to about 3M.

As indicated above, the gel formation procedure is conducted under conditions in which substantially no electroosmotic flow or driving force occurs. Thus, either the capillary itself or the liquid species occupying its interior are selected or treated such that little or no electrokinetic potential is present. This is achieved by methods known to those skilled in the art. These methods generally follow one of two basic approaches. The first is the chemical bonding of a neutral material to the inner surface of the capillary to eliminate surface charge and adsorption sites. The second involves the manipulation of buffer pH and ionic strength to reduce or eliminate the electrokinetic effect.

The first approach is preferred for the present invention. Various neutral materials and methods of bonding such materials to the capillary surface may be used. For silica-containing surfaces, examples are the bonding of glycol-containing materials, the bonding of linear polymers such as methyl cellulose and noncrosslinked polyacrylamide through an organosilane reagent, the application of a poly(vinylpyrolidinone) coating, also optionally done through an organosilane reagent, and the use of polyethyleneglycol. Many of these coating techniques are documented in the literature and known among those skilled in the art.

The chemical composition and structure of the capillary itself is not critical, and can vary widely. Preferred capillaries are those of silica-containing materials, such as glass, fused silica and quartz. Fused silica is particularly convenient due to its wide availability and proven performance.

The dimensions of the capillary may also vary widely. In most cases, the capillary will have an internal diameter ranging from about 5 microns to about 250 microns, preferably from about 20 microns to about 100 microns. Likewise, the length of the capillary will in most cases range from about 5 cm to about 500 cm, preferably from about 10 cm to about 100 cm.

The electric field is imposed across the capillary by conventional techniques. The process is particularly well adapted to such techniques as are used in the electrophoretic separation itself. This generally involves immersing the two ends of the capillary in solutions retained in reservoirs, each further containing one of the two electrodes. The electric potential is then applied between the electrodes from a conventional power source. An illustration of this arrangement is shown in FIG. 1, which shows the capillary tube 11 with its two open ends 12, 13 immersed in separate electrode reservoirs 14, 15, with the electrodes 16, 17 immersed therein as well. Power is supplied to the electrodes by a power source 18. As a typical example, the cathodic reservoir 14 contains persulfate ion, and the anodic reservoir 15 contains triethanolammonium ion, while the capillary, prior to the imposition of the electric potential, is filled with a mixture of acrylamide, N,N'-methylenebisacrylamide, and triethanolamine hydrochloride.

The magnitude of the electric potential is not critical. The primary consideration will be the avoidance of excessive Joule heating occurring in the capillary as a result of the current. While the Joule heating can be lessened by cooling through the capillary walls, in most cases it will be impractical to contact the outer capillary surface with a liquid coolant medium. Accordingly, Joule heating is generally controlled by limiting the voltage. In most cases, the potential will be within the range of from about 0.5V to about 20V per centimeter of capillary length, preferably from about 1.0V to about 10V per centimeter of capillary length.

It is also of concern that the potential be low enough to provide for a slow and steady movement of the initiator front through the capillary interior, in a manner which promotes the maintenance of a front which is as sharp an increase in initiator concentration as possible. The purpose of this is to assure to the greatest extent possible that polymerization occurs quickly with reference to the linear velocity of the front, thereby restricting all fluid motion due to shrinkage to the nonpolymerized regions ahead of the front. The optimal potential and hence front velocity will vary with the particular system, including the type of gel monomer and cross-linking agent and their concentrations. In most cases, best results will be achieved with a front moving at a linear velocity of from about 0.003 cm/min to about 0.3 cm/min, preferably from about 0.01 cm/min to about 0.1 cm/min.

Once the gel has been formed to the desired degree of polymerization, it is preferable to remove all nonpolymerized components used for gel formation, such as the initiator and catalyst, from the gel. This is readily achieved by replacing the solutions in the electrode reservoirs with the background electrolyte to be used in subsequent electrophoretic separations. This will vary depending on the separation intended to be performed, but the procedure is standard and applicable to all such electrolytes. Voltage is applied to sweep the electrolyte through the gel and thereby remove the initiator and catalyst. Once again, the primary consideration is the avoidance of excessive Joule heating which might cause the gel to decompose. This equilibration procedure can be monitored by an on-line detector such as a UV detector, which will indicate a stabilized base line once all moving boundaries have passed through the capillary.

Capillary gels formed in accordance with this invention are useful in performing a wide variety of separations, including those previously performed in capillary tubes and those performed in gel media. Such separations include, but are not limited to, separations of proteins, peptides, oligonucleotides, and oligosaccharides.

The following example is offered for purposes of illustration, and is intended neither to define nor limit the invention in any manner.

EXAMPLES A. Capillary Coating.

A 40-cm length of fused silica capillary tubing (50 μm internal diameter, 187 μm outer diameter, Polymicro Technologies, Phoenix, Az., U.S.A.) was rinsed sequentially with 1M NaOH and distilled water for thirty minutes each. The capillary was filled with a solution prepared from 4μL of γ-methacryloxypropyltrimethoxysilane in 1 mL of 6 mM acetic acid. After at least one hour, the capillary was rinsed with distilled water for several minutes, then emptied. The capillary was then filled with a deaerated solution of 2.5% acrylamide containing 0.1% ammonium persulfate and 0.1% N,N,N',N'-tetramethylethylenediamine (TEMED). After thirty minutes, the capillary was rinsed with distilled water for 5 minutes, then emptied.

B. Gel Formation.

The coated capillary was filled with a mixture containing 5.8% acrylamide (T=6%), 0.18% N,N'-methylene-bisacrylamide (C=3%), and 100 mM triethanolamine hydrochloride. One end of the capillary was placed in a vial containing 10% ammonium persulfate and a platinum wire electrode. The other end of the capillary was placed in a vial containing 25% triethanolamine and a second platinum wire electrode. The electrodes were connected to a low-voltage dc power supply with the first electrode as the anode and the second as the cathode, and a potential of 160V (i.e., 4V/cm) was applied for eight to fifteen hours.

The cathodic and anodic vials were then replaced by vials containing the background buffer to be used in the electrophoretic separation, the buffer including 100mM tris(hydroxymethyl)aminomethane, 200mM 2-(N-morpholino)-ethanesulfonic acid, and 1% sodium dodecyl sulfate. High voltage (500V) was then applied for about five hours, followed by a step-wise increase in the voltage such that the Joule heating generated in the capillary did not exceed 0.5 mW/cm. This equilibration with background buffer was continued until the current stabilized at a steady voltage and an on-line variable wavelength UV-absorbance detector (UVIDEC 100 IV, Jasco, Tokyo, Japan), which was aligned with a section of the capillary from which the polymer coating had been removed, located approximately 15 cm from one end, gave a stabilized baseline indicating that all moving boundaries had passed.

C. Use of Gel-Filled Capillary in Separation of Proteins

Figure 2:
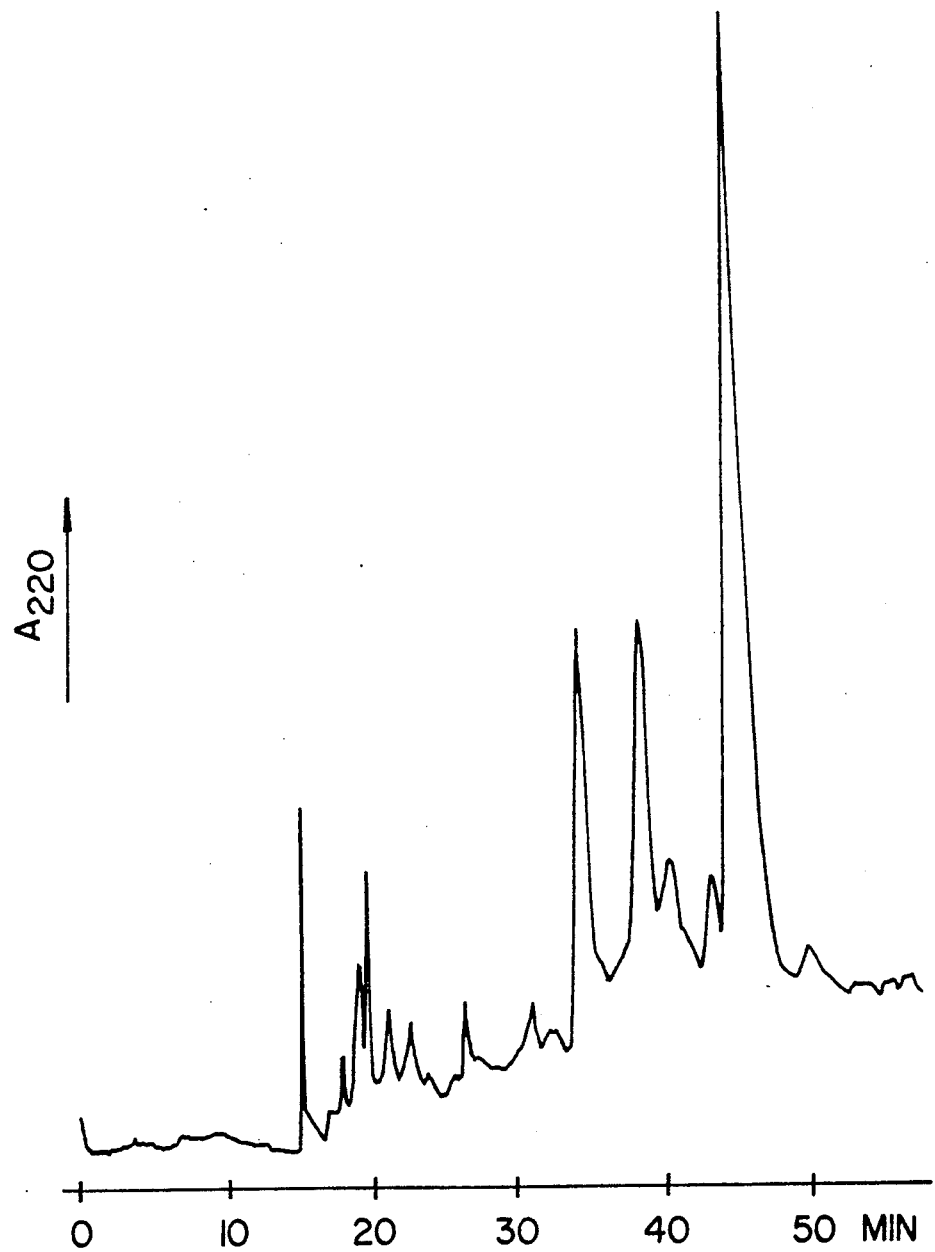
FIG. 2 is a trace from a detector of a capillary gel electrophoretic separation of proteins in untreated mouse urine using a gel-filled capillary prepared in accordance with the invention.

Electrophoresis of a sample of untreated mouse urine was performed in a 35-cm length of the gel-filled capillary of Section B of this example. The length of the capillary up to the detector was 20 cm, and the detector identified in Section B was used. The background electrolyte was identical to that described above, with 0.1–1.0% sodium dodecyl sulfate. Samples were introduced by electromigration for 5–60 seconds at 100V/cm. The resulting detector trace is shown in FIG. 2, which is in conformance with analyses generated otherwise of sample from the same source.

D. Use of Gel-Filled Capillary in Separation of Oligosaccharides

A capillary prepared in an analogous manner was used for oligosaccharide separation. The capillary had an internal diameter of 100 μm and a length of 27 cm, of which 19 cm was the effective length. The gel materials and polymerization procedure were the same as those described in Sections A and B above, and the final gel was characterized by T=10%, C=3%. The buffer was 0.1M Tris/0.25M borate/7M urea at pH=8.33.

Figure 3A:
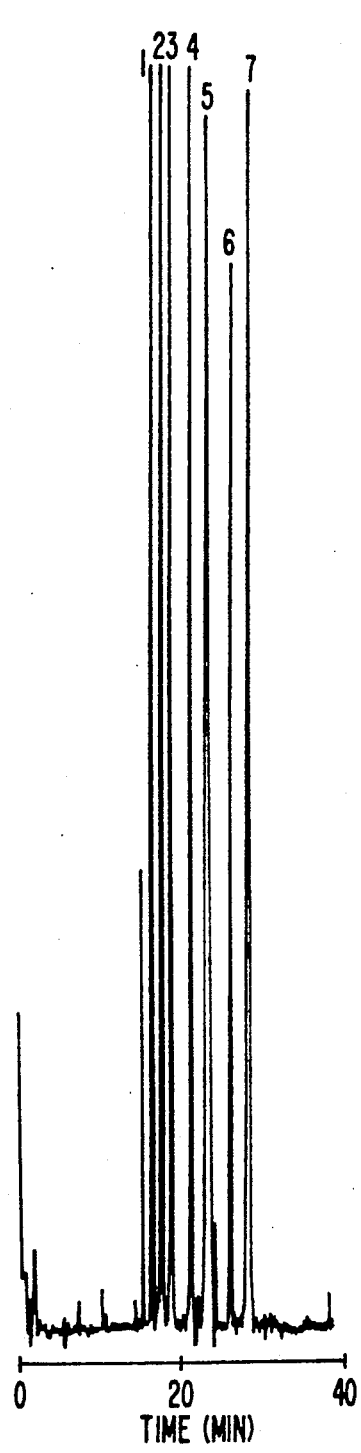
FIGS. 3a and 3b are traces from a detector of a capillary gel electrophoretic separation of oligosaccharides, again using a gel-filled capillary prepared in accordance with the invention.

The first sample separated consisted of a mixture of the following:
1. glucose
2. maltose
3. maltotriose
4. maltotetraose
5. maltopentaose
6. maltohexaose
7. maltoheptaose Each species was reductively animated and tagged with an amine-selective fluorogenic reagent prior to separation, to permit detection by laser-induced fluorescence. Injection was achieved by electromigration at 3 kV for 10 sec. For the separation, the applied voltage was 7 kV (264V/cm) at 18 $\mu$A. The resulting detector trace is shown in FIG. 3a, in which the peaks are identified by the numbers listed above.

Figure 3B:
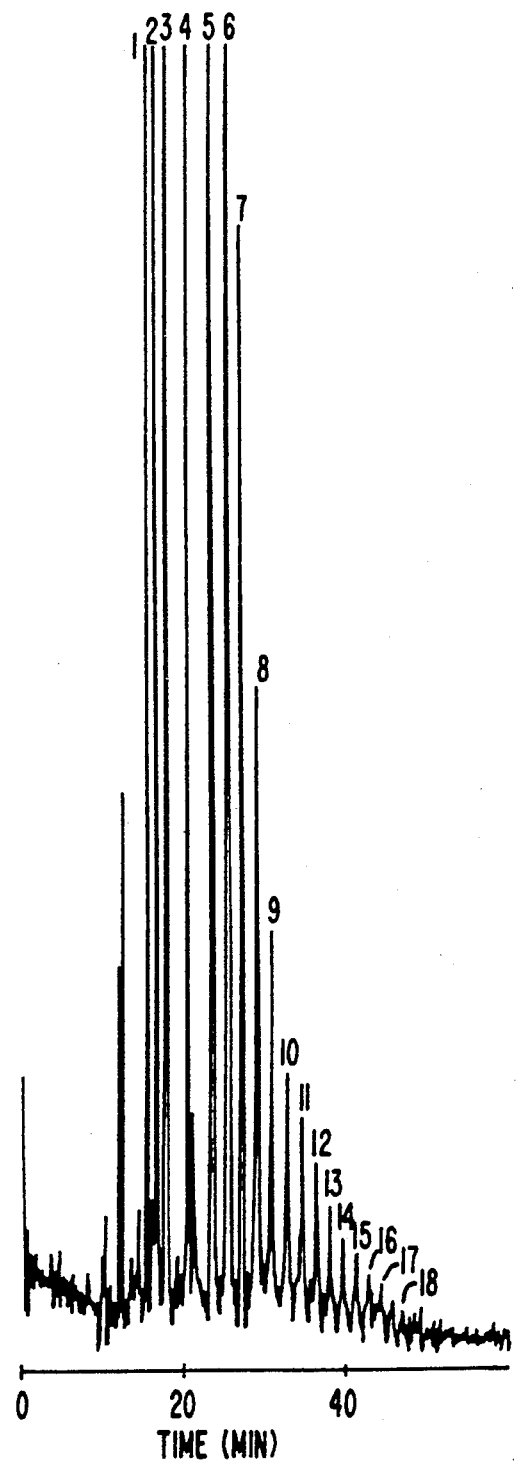

The second sample separated consisted of a mixture resulting from the partial hydrolysis of the polysaccharide maltodextrose (Dextrin 15), animated and tagged in the same manner as the oligosaccharides of the first sample. Injection was achieved by electromigration at 5 kV for 30 sec, and the separation was performed with an applied voltage of 7 kV (264V/cm) at 18 $\mu$A. The resulting detector trace is shown in FIG. 3b, in which the peaks are numbered to represent the observed oligomers.

E. Use of Gel-Filled Capillary in Separation of Oligonucleotides

A further capillary, also prepared in an analogous manner, was used for the separation of a polynucleotide mixture consisting of pd(A)$_{25-30}$ and pd (A)$_{40-60}$. The capillary had an internal diameter of 75 $\mu$m and a length of 27 cm, of which 20 cm was the effective length. The gel materials and polymerization procedure were the same as those described in Sections A and B above, and the final gel was characterized by T=10%, C=5%. The buffer was 0.1M Tris-borate/7M urea at pH=8.1, and the applied voltage was 7.5kV, 3$\mu$A.

Figure 4:
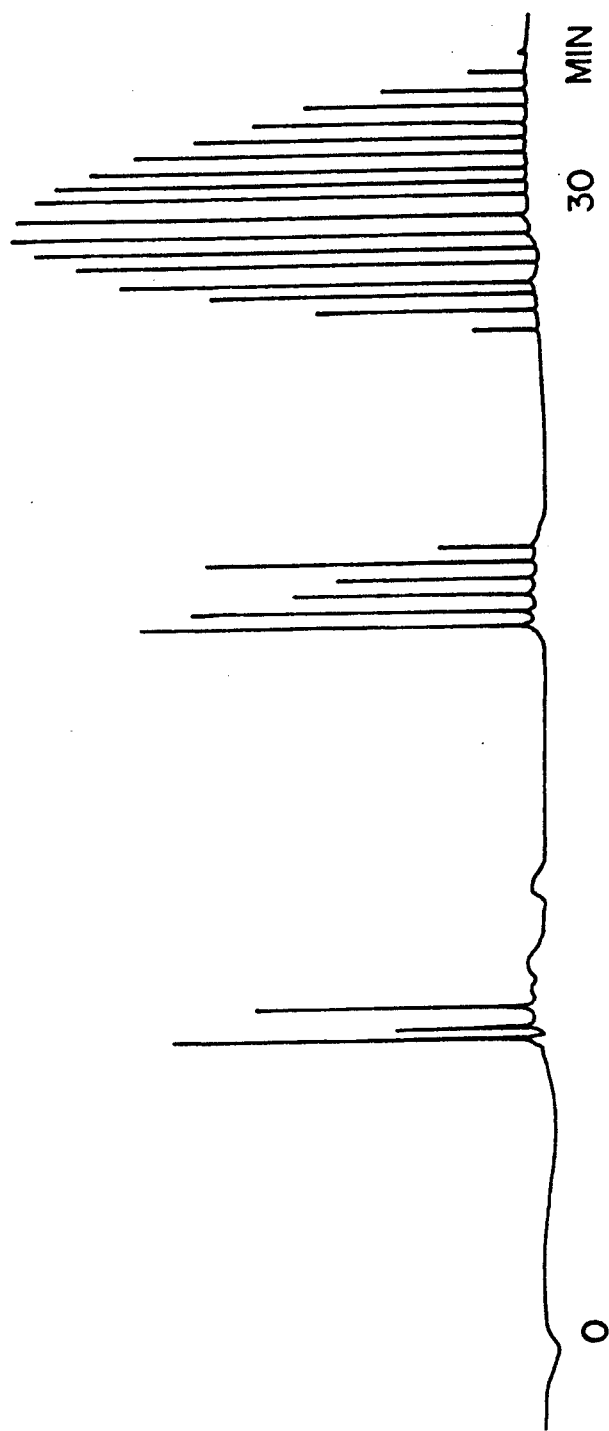
FIG. 4 is a trace from a detector of a capillary gel electrophoretic separation of oligonucleotides, again using a gel-filled capillary prepared in accordance with the invention.

The results are shown in FIG. 4, which indicates that clean separations were achieved.

The foregoing is offered primarily for purposes of illustration. It will be readily apparent to those skilled in the art that numerous variations and substitutions in both the materials and procedures disclosed herein may be made without departing from the spirit and scope of the invention.

What is claimed is:

1. A method for preparing a gel-filled capillary column for use in capillary electrophoresis, said method comprising:
   (a) filling a capillary tube having first and second ends with a solution of gel-forming material capable of undergoing a gel-forming polymerization reaction when placed in contact with a polymerization initiator;
   (b) immersing said first end of said capillary tube in a first electrode solution in which is dissolved said polymerization initiator in a form susceptible to migration when exposed to an electric field, and immersing said second end of said capillary tube in a second electrode solution; and
   (c) imposing an electric potential between said first and second electrode solutions through said capillary tube, under conditions substantially free of electroosmotic flow, to cause migration of said polymerization initiator into said capillary tube led by a front of said polymerization initiator traveling along said capillary tube from said first end to said second end at a predetermined linear velocity, thereby causing said polymerization reaction to occur along said front.

2. A method in accordance with claim 1 in which said polymerization initiator is a free radical initiator.

3. A method in accordance with claim 2 in which said free radical initiator is a member selected from the group consisting of peroxides, persulfates and azo compounds.

4. A method in accordance with claim 2 in which said free radical initiator is persulfate ion.

5. A method in accordance with claim 2 in which said free radical initiator is persulfate ion, and the concentration of said persulfate ion in said first electrode solution is from about 0.03M to about 2.0M.

6. A method in accordance with claim 2 in which said free radical initiator is persulfate ion, and the concentration of said persulfate ion in said first electrode solution is from about 0.1M to about 1.0M.

7. A method in accordance with claim 1 in which said gel-forming material is comprised of a polyacrylamide precursor.

8. A method in accordance with claim 1 in which said gel-forming material is comprised of a polyacrylamide precursor, a crosslinking agent and a base.

9. A method in accordance with claim 1 in which said gel-forming material is comprised of acrylamide monomer, a crosslinking agent and a base, and said second electrode solution is a solution of said base.

10. A method in accordance with claim 1 in which said capillary tube is a fused silica capillary, the internal surface of which is coated with an electroosmosis-suppressing substance.

11. A method in accordance with claim 1 in which said capillary tube has an internal diameter of from about 5 microns to about 250 microns.

12. A method in accordance with claim 1 in which said capillary tube has an internal diameter of from about 20 microns to about 100 microns.

13. A method in accordance with claim 1 in which said electric potential of step (c) is from about 0.5 to about 20V per cm length of said capillary tube.

14. A method in accordance with claim 1 in which said electric potential of step (c) is from about 1.0 to about 10V per cm length of said capillary tube.

15. A method in accordance with claim 1 in which said predetermined linear velocity of step (c) is from about 0.003 to about 0.3 cm/min.

16. A method in accordance with claim 1 in which said predetermined linear velocity of step (c) is from about 0.01 to about 0./1 cm/min.

17. A method in accordance with claim 9 in which said base is an amine.

18. A method in accordance with claim 9 in which said base is an amine selected from the group consisting of N,N,N',N'-tetramethylethylenediamine, $\beta$-dimethylamino-propionitrile, and triethanolamine.

* * * * *